United States Patent [19]

Schmidt et al.

[11] Patent Number: 5,507,079
[45] Date of Patent: Apr. 16, 1996

[54] NARROW FIBERGLASS KNIT TAPE

[75] Inventors: Jacquelyn A. Schmidt, St. Paul, Minn.; John M. Kokorudz, Lake Forrest, Calif.; Matthew T. Scholz, Woodbury, Minn.; Miroslav M. Tochacek, Woodbury, Minn.; F. Andrew Ubel, III, St. Paul, Minn.

[73] Assignee: Minnesota Mining and Manufacturing Company, St. Paul, Minn.

[21] Appl. No.: 284,200

[22] Filed: Aug. 2, 1994

Related U.S. Application Data

[62] Division of Ser. No. 976,402, Nov. 13, 1992, Pat. No. 5,353,480.

[51] Int. Cl.$^6$ .............. C08G 73/10; D06H 7/00; A61F 5/00
[52] U.S. Cl. .................. 28/170; 66/202; 602/8
[58] Field of Search ............. 66/202, 194, 195; 28/170; 602/8

[56] References Cited

U.S. PATENT DOCUMENTS

| | | | |
|---|---|---|---|
| 2,592,153 | 4/1952 | Johnson et al. | 28/168 |
| 2,609,569 | 9/1952 | Walter et al. | 18/54 |
| 2,653,466 | 9/1953 | McCusker | 68/178 |
| 3,686,725 | 8/1972 | Nisbet et al. | 28/74 R |
| 3,787,272 | 1/1974 | Nisbet et al. | 161/89 |
| 3,793,686 | 2/1974 | Nisbet et al. | 28/75 R |
| 3,848,556 | 11/1974 | Terada et al. | 112/265 |
| 3,859,825 | 1/1975 | Foulquies et al. | 66/192 |
| 3,945,096 | 3/1976 | Miranker | 28/76 T |
| 4,265,003 | 5/1981 | Matsuda | 66/195 X |
| 4,370,871 | 2/1983 | Nakagaki et al. | 66/202 |
| 4,376,438 | 3/1983 | Straube et al. | 128/90 |
| 4,400,418 | 8/1983 | Takeda et al. | 66/194 X |
| 4,411,262 | 10/1983 | von Bonin et al. | 128/90 |
| 4,433,680 | 2/1984 | Yoon | 128/90 |
| 4,502,479 | 3/1985 | Garwood et al. | 128/90 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,745,912 | 5/1988 | McMurray | 66/202 X |
| 4,759,106 | 7/1988 | McPeak et al. | 28/168 |
| 5,014,403 | 5/1991 | Buese | 28/170 |

FOREIGN PATENT DOCUMENTS

| | | | |
|---|---|---|---|
| 2452541 | 10/1980 | France | 66/196 |
| 3805234 | 8/1989 | Germany . | |
| 0143750 | 12/1978 | Japan | 28/168 |
| 612495 | 11/1948 | United Kingdom | 28/168 |
| 2189421 | 10/1987 | United Kingdom | 28/168 |

OTHER PUBLICATIONS

Raschel Lace Production by B. Wheatley pp. 1–15 and 144–152.
European Search Report.

*Primary Examiner*—John J. Calvert
*Attorney, Agent, or Firm*—Gary L. Griswold; Walter N. Kirn; F. Andrew Ubel

[57] ABSTRACT

The present invention provides a narrow orthopedic casting tape which can be handled in longer lengths suitable for economical production of coated fabric products. The narrow casting tape of the present invention is knitted as a wide fiberglass fabric with at least one removable connecting yarn in the length (i.e., warp) direction of the fabric which acts to connect two narrower strips of fiberglass fabric. The removable connecting yarn is subsequently removed from the fabric by a heat treatment process which separates the wider fabric into two narrower fabrics and also heat sets the fabric. Alternatively, the removable connecting yarn may be removed from the fabric by a dissolution process. Narrow fabrics of the present invention can also be constructed of organic yarns.

The present invention also provides a tearable orthopedic casting tape which has a high degree of extensibility. The tearable casting tape of the present invention is knitted as a wide fabric, preferably fiberglass, with at least one tearable connecting yarn in the length direction of the fabric which acts to weakly connect two or more narrower fabrics. The tearable connecting yarn is capable of being easily torn or slit causing the fabric to separate into narrower webs.

12 Claims, 3 Drawing Sheets

NARROW FIBERGLASS KNIT TAPE

This is a division of application Ser. No. 07/976,402 filed Nov. 13, 1992, now U.S. Pat. No. 5,353,480.

FIELD OF THE INVENTION

This invention relates to the field of knitted fiberglass fabrics. More particularly, it relates to a method of forming narrow knitted fiberglass fabrics. More particularly, it relates to extensible knitted fiberglass fabrics which are coated or impregnated with a liquid resin which cures to form rigid reinforced fiberglass articles. Another aspect of the invention relates to a wide knitted fiberglass fabric which may be easily separated (e.g., torn) into two or more narrower fiberglass fabrics. A preferred embodiment of the invention relates to orthopedic casting tapes comprising resin-coated or impregnated, extensible, knitted fabrics.

BACKGROUND OF THE INVENTION

Plaster of Paris casts have been in use to immobilize body members or limbs for some time. In recent years, the plaster of Paris bandages have been superseded by synthetic casting tapes which employ polymeric materials on a fiberglass substrate. The polymeric materials are of the type that cure by exposure to actinic radiation or cure when reacted with water. More recently, water-cured or water-reactive polyurethane compositions have been used in forming orthopedic casts and the polyurethane compositions have largely supplanted other polymeric synthetic casting materials. The polyurethane casting materials are of the type which are disclosed in U.S. Pat. Nos. 4,667,661; 4,609,578; 4,411,262; and 4,376,438.

High modulus fibers such as fiberglass are commonly used as resin reinforcements in composite materials to impart strength to the cured article. In some applications the fiberglass yarn is woven or knit into a fabric which can then be treated with a finish, resin or other coating. Compared to organic fibers such as polyester, glass fibers virtually no elongation and are more prone to breakage during process operations such as knitting and weaving. Because the fiber elongation is essentially nil, glass fabrics do not stretch unless they are constructed with very loose loops which can deform upon application of tension, thereby providing stretching of the fabric. Knitting with loosely formed chain stitches imparts extensibility by virtue of its system of interlocking knots and loose loops.

An important usage of knitted fiberglass fabrics is in the manufacture of orthopedic cast bandages where those fabrics are coated or impregnated with a curable resin and packaged as rolls of casting tape, which are subsequently used by a physician or medical clinician to construct orthopedic casts. When constructing an orthopedic cast from a roll of casting tape (typically ~100 millimeters (mm) wide), it is necessary to change the direction of wrapping to accommodate body contours such as the heel of the foot. This requires a high level of skill on the pan of the applier to achieve a functional and smooth cast. To facilitate application, it is desirable that the bandaging material be extensible. At least 20% and preferably 25%–35% extensibility is necessary in material of 100 mm width to conform easily around the heel of a medium size adult.

Like most knitted fabrics, fiberglass knits tend to curl or fray at a cut edge as the yarns are severed and adjacent loops unravel. Fraying and raveling produce unsightly ends and, in the case of an orthopedic cast, frayed ends may interfere with the formation of a smooth cast, and loose, frayed ends may be sharp and irritating after the resin thereon has cured. Accordingly, frayed edges are considered a distinct disadvantage in orthopedic casting tapes.

Stretchy fiberglass fabrics which resist fraying are disclosed in U.S. Pat. No. 4,609,578 (Reed), the disclosure of which is incorporated by reference. Thus, it is well known that fraying of fiberglass knits at cut edges can be reduced by passing the fabric through a heat cycle which sets the yarns giving them new three-dimensional configurations based on their positions in the knit. Fiberglass fabrics intended to be coated or impregnated with a resin are sometimes put through a heat-setting process for the additional purpose of removing sizing from glass filaments which may otherwise interfere with the proper application of the resin.

A batch process recommended by Owens-Corning Fiberglass Corporation, Toledo, Ohio to remove the sizing on the glass filaments results in a heat-set fabric and consists of the following steps:

1. Start at 100° C. for 1.5 hours;
2. Raise to 250° C. over a period of 5 hours and hold for 12 hours;
3. Raise to 370° C. over a period of 3 hours and hold for 33 hours;
4. Cool to room temperature.

A continuous process involving much less time is also possible.

When a fiberglass fabric which has been heat-set is cut, there is minimal fraying and when a segment of yarn is removed from the heat-set fabric and allowed to relax, it curls into the crimped shape in which it was held in the knit. Accordingly, at the site of a cut, the severed yarns have a tendency to remain in their looped or knotted configuration rather than to spring loose and cause fraying.

In processing extensible fiberglass fabrics according to U.S. Pat. No. 4,609,578 (Reed), a length of fabric is heat-set with essentially no tension. The fabric is often wound onto a cylindrical core so large batches can be processed at one time in a single oven. Care must be taken to avoid applying undue tension to the fabric during wind-up on the knitter which would distort the knots and loops. To prevent applying tension to the fabric during winding, the winding operation is preferably performed with a sag in the fabric as it is wound on the core.

Prior to the present invention, rolls of moving webs of fabric were typically either (1) wound with some degree of tension (thereby distorting the knots and loops) or (2) wound loosely in the form of a wide web (e.g., >50 mm width) so that the roll would not telescope and the web could be steered and uniformly processed. Unfortunately, narrow webs (i.e., webs having a width less than about 50 mm) easily telescope or collapse when wound loosely on the core and also easily "neck-down" (i.e., the narrow web distorts forming a narrower than desired width) in response to even minimal knitting or winding forces which are transmitted to the free edges of the tape. Wide webs are also susceptible to neck-down. These problems have made it difficult to and greatly increased the cost of producing narrow webs with good extensibility and webs of uniform width.

SUMMARY OF THE INVENTION

The present invention provides a narrow orthopedic casting tape which has a high degree of extensibility and can be handled in longer lengths suitable for economical production of coated fabric products. The narrow casting tape of the present invention is knitted as a wide fiberglass fabric with at least one removable connecting yarn in the length (i.e., warp) direction of the fabric which acts to connect two narrower strips of fiberglass fabric. The wider fabric is first formed and wound around a core, then removable connecting yarn is subsequently removed from the fabric by a heat treatment process which separates the wider fabric into two narrower fabrics and also heat sets the fabric. Alternatively, the removable connecting yarn may be removed from the fabric by a dissolution process. By either method of removal, removal of one (or more) such removable connecting yarn(s) causes the wider fabric to separate into two (or more) narrower fabrics.

The presence of the removable connecting yarns between the strips of the knitted fiberglass fabric allows the fabric to be handled normally, i.e., allowing nearly tension free winding, until the fabric is heat set. The presence of the removable connecting yarn in the knitted fiberglass fabric also resists neck-down of the fabric as it comes off the needle bed and controls the uniformity of the fabric width for wide or narrow fabrics.

Narrow fabrics of the present invention can also be constructed of organic yarns. Such narrow casting tape of the present invention is also knitted as a wide fabric with at least one removable connecting yarn in the length direction of the fabric which acts to connect two narrower fabrics. The removable connecting yarn is subsequently removed from the organic fabric by a dissolution process. The removal of the removable connecting yarn(s) causes the fabric to separate into narrower webs. The presence of the removable connecting yarn in the knitted fabric allows the fabric to be handled normally and to resist necking-down thereby controlling the uniformity of the fabric width.

The present invention also provides a tearable orthopedic casting tape which has a high degree of extensibility. The tearable casting tape of the present invention is knitted as a wide fabric, preferably fiberglass, with at least one tearable connecting yarn in the length direction of the fabric which acts to weakly connect two or more narrower fabrics. The tearable connecting yarn is capable of being easily torn or slit causing the fabric to separate into narrower webs. The presence of the tearable connecting fiber in the knitted casting fabric allows the fabric to be handled normally and be wrapped onto the limb as a wide casting tape. When desired this wide casting tape may be easily torn into narrower strips and wrapped around small projections such as a thumb or a pin.

DETAILED DESCRIPTION OF THE INVENTION

The substrate of the casting tape of the present invention is preferably knitted with a combination of organic and inorganic yarns. The yarns are fabricated from multiple individual organic fibers or inorganic fibers or both. As used herein "fiber" refers a slender and greatly elongated natural or synthetic filament capable of being spun or formed into yarn. Casting tape substrates are often characterized as made from inorganic (e.g., glass) fibers or filaments which are formed into yarn, sized and knitted into a desired fabric. Alternatively, casting tapes of the present invention may be made exclusively from organic yarns.

In the present invention the substrates are presently preferably knitted on a Raschel Knitting Machine having 2 to 13 needles per centimeter (cm). The cast substrate fabrics of the present invention are knitted fabrics which may include, for example, an inorganic yarn (e.g., comprising high modulus fiberglass), an organic yarn (e.g., comprising polyester fibers), or a combination of the two when the fabric is knitted.

Yarns are generally structures with a high degree of fiber orientation with respect to the principal axis of the material. The degree of fiber parallelism and orientation varies from one type of yarn to another, and can be controlled by fiber type and processing. Spun yarns are produced from fibers by a combination of processing steps referred to collectively as yarn spinning. After preliminary fiber alignment, the fibers are locked together by twisting the structure to form the spun yarn which is continuous in length and substantially uniform. Yarns produced from continuous filament synthetic fibers (e.g., fiberglass) are called multifilament yarns and are characterized by nearly complete filament alignment and parallelism with respect to the yarn axis. The degree of twist is usually quite low and just adequate to produce some interfilament cohesion.

When used as a connecting yarn, the yarn may be comprised of any suitable combustible, dissolvable or tearable organic fiber or tearable inorganic fiber. Suitable organic fibers include synthetic polymer fibers as well as natural organic fibers. The organic fiber may also comprise natural rubber or a synthetic elastomer although these are not preferred.

Suitable synthetic polymer connecting fibers include; naturally based organic polymers such as acetate, azlon, rayon, and triacetate; and synthetically prepared organic polymers such as acrylic, aramid, nylon, olefin (e.g., poly(1-butene), polyethylene, poly(3-methyl-1-butene), poly(1-pentene), polypropylene, and polystyrene), polyester, polytetrafluoroethylene, poly(vinyl alcohol), poly(vinyl chloride), and poly(vinylidine chloride). Preferred synthetic polymer fibers include; acetate, acrylic, nylon, polyethylene, polypropylene, polyester, and rayon. Most preferred synthetic polymer fibers include; acetate, acrylic, nylon, polyester, and rayon.

Suitable natural organic connecting fibers include: vegetable derived materials such as abaca, cotton, flax, hemp, jute, kapok, linen, ramie, and sisal; and animal derived materials such as wool, mohair, vicuna, other animal hairs, and silk. Preferred natural organic fibers include: cotton and wool. Cotton is most preferred.

Suitable elastomeric connecting fibers include natural rubber, polyisoprene, polybutadiene, diene styrene copolymers, ethylene propylene copolymers, ethylene propylene diene terpolymers, styrene butadiene block copolymers, styrene isoprene block copolymers, and polyurethanes such as spandex.

Suitable inorganic connecting fibers include glass, metallic, and ceramic fibers.

The yarns of the fabric itself may be comprised of any suitable high-strength high-modulus fiber or filament. Preferred fabric yarns comprise polymer fibers (e.g., polyester) as well as inorganic fibers such as glass, metal, and ceramic fibers. Glass fibers are presently most preferred.

Fiberglass knitted fabrics with good extensibility are achievable with two common knitting methods: Raschel and tricot. Raschel knitting is described in "Raschel Lace Production" by B. Wheatley (published by the National Knitted Outerwear Association, 51 Madison Avenue, New York, N.Y. 10010) and "Warp Knitting Production" by Dr. S. Raz (published by Heidelberger Verlagsanstadt und Druckerei GmbH, Hauptstr. 23, D-6900 Heidelberg, Germany). Two, three and four bar Raschel knits can be produced by regulating the amount of yarn in each stitch. Orthopedic casting tape fabrics are preferably two bar Raschel knits although extra bars may be employed. Factors which affect the extensibility of fiberglass Raschel knits are the size of the loops in the "chain" stitch, especially in relation to the diameter(s) of the yarn(s) which passes through them, and the amount of a loose yarn in the "layin" or "laid-in" stitch(es). If a chain loop is formed and two strands of layin yarn pass through it which nearly fill the loop, then the loop resists deformation and little stretch will be observed. Conversely, if the layin yarns do not fill the loop, then application of tension will deform the loop to the limits of the layin yarn diameter and stretch will be observed.

Typical bar patterns for the knit fabric substrates of the present invention are shown in the drawings.

Figure 1:
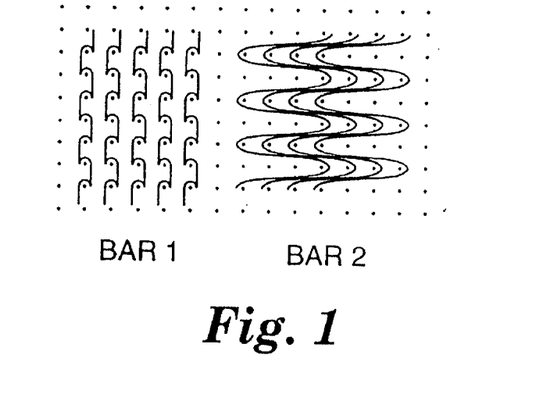
FIG. 1 is a two bar Raschel knit in which bar 1 performs a simple chain stitch and bar 2 performs lapping motions to lay in yarn.

FIG. 1 is a two bar Raschel knit in which bar 1 performs a simple chain stitch and bar 2 performs lapping motions to lay in yarn.

Figure 2:
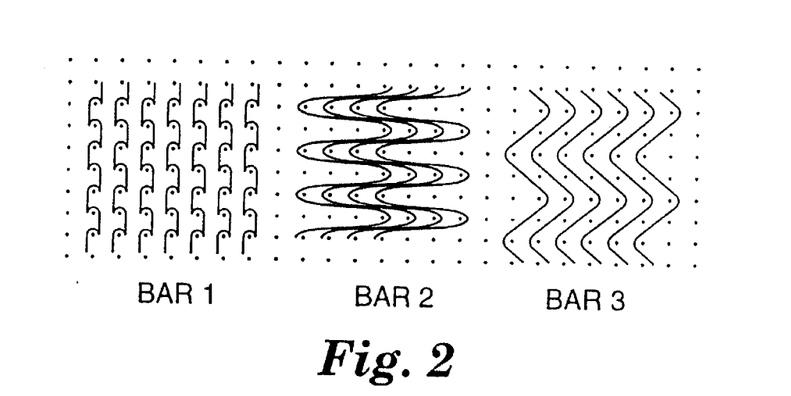
FIG. 2 is a three bar Raschel knit in which bar 1 performs a simple chain stitch and bars 2 and 3 perform lapping motions to lay in yarn.

FIG. 2 is a three bar Raschel knit in which bar 1 performs a simple chain stitch and bars 2 and 3 perform lapping motions to lay in yarn.

Figure 3:
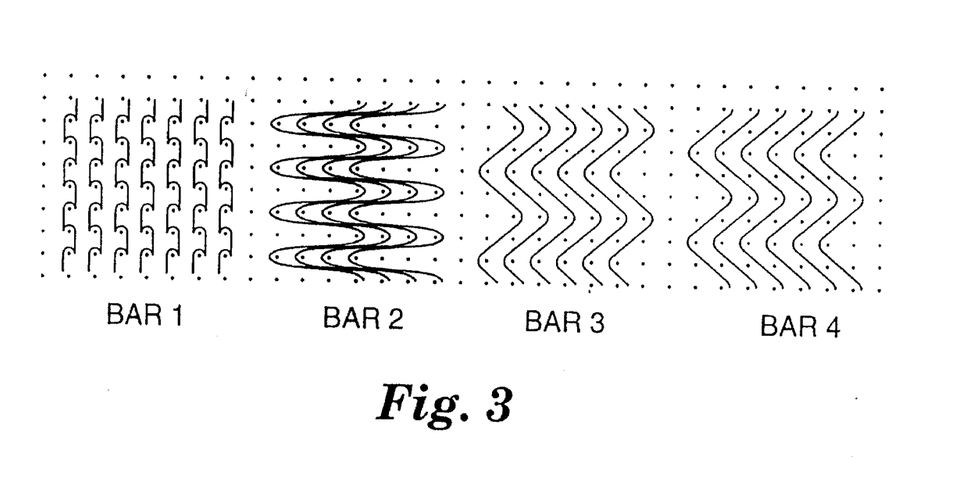
FIG. 3 is a four bar Raschel knit in which bar 1 performs a simple chain stitch and bars 2, 3 and 4 perform lapping motions to lay in yarn.

FIG. 3 is a four bar Raschel knit in which bar 1 performs a simple chain stitch and bars 2, 3 and 4 perform lapping motions to lay in yarn.

Figure 4:
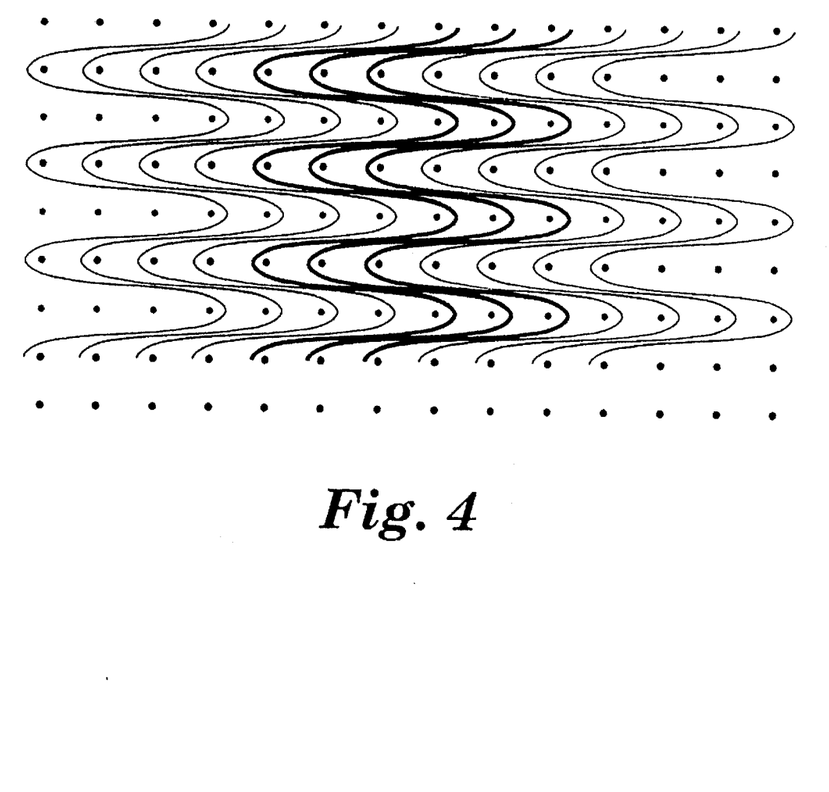
FIG. 4 is a depiction of bar 2 of a two, three or four bar Raschel knit in which the yarns comprise either fabric yarns (shown as lightweight lines) or connecting yarns (shown as heavyweight lines).

FIG. 4 is a depiction of bar 2 of a two, three or four bar Raschel knit in which the yarns comprise either fabric yarns (shown as lightweight lines) or connecting yarns (shown as heavyweight lines).

Figure 5:
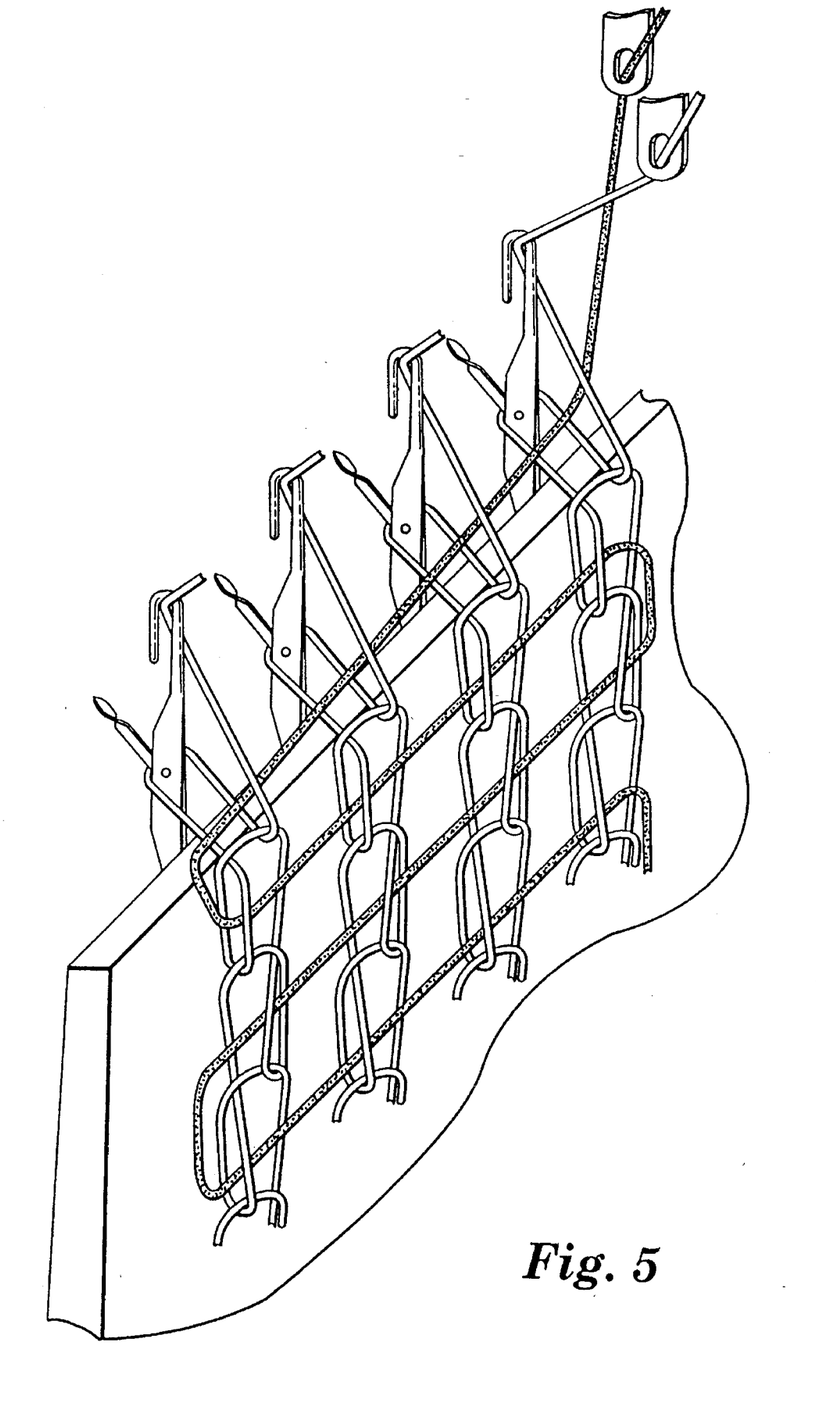
FIG. 5 is a depiction of a two bar "latch hook" Raschel knitter in which four needles are shown knitting four chain stitches and a lay in stitch. For the purposes of this invention, one might alternatively employ a "compound needle" Raschel knitter which is not shown.

FIG. 5 is a depiction of a two bar "latch hook" Raschel knitter in which four needles are shown knitting four chain stitches and a lay in stitch. For the purposes of this invention, one might alternatively employ a "compound needle" Raschel knitter which is not shown.

Figure 6:
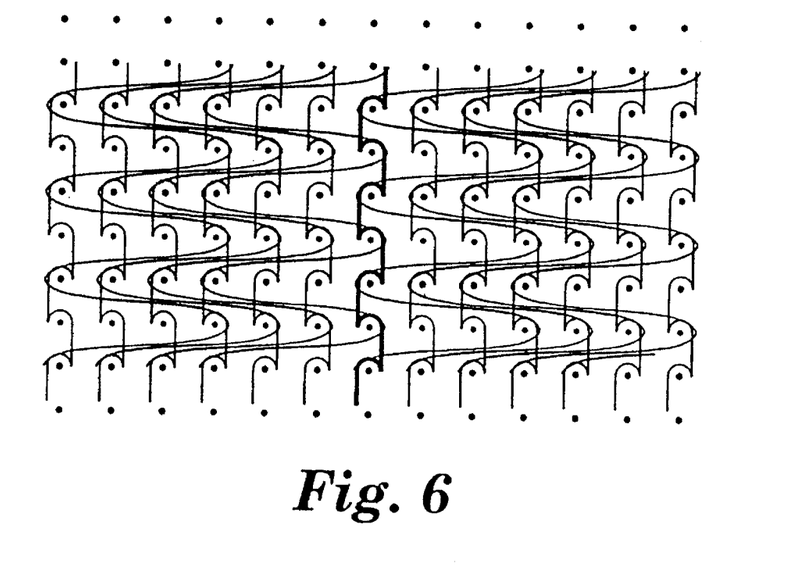
FIG. 6 is a depiction of a two bar Raschel knit in which bar 1 performs a simple chain stitch and bar two performs lapping motion to lay in yarn. The bars are depicted in a overlapping view and further depict a chain stitch connecting yarn (shown as a heavyweight line).

FIG. 6 is a depiction of a two bar Raschel knit in which bar 1 performs a simple chain stitch and bar two performs lapping motion to lay in yarn. The bars are depicted in a overlapping view and further depict a chain stitch connecting yarn (shown as a heavyweight line). It should be understood that the above bar patterns may be modified. For example, the lay in stitches could be made to overlap additional chain stitches.

For orthopedic casting material, the fabric selected (preferably fiberglass), in addition to having the extensibility requirement noted above, should be of a suitable thickness and mesh size to insure good penetration of the curing agent into the roll of resin-coated tape and to provide a finished cast with adequate strength and porosity. Such fabric parameters are well-known to those skilled in the art and are described in U.S. Pat. No. 4,502,479 which is herein incorporated by reference.

The present invention provides wide knit fabrics comprising one or more connecting yarns which connect two or more narrower fabrics. Preferably, the narrower fabrics are made of inorganic yarns such as fiberglass. The connecting yarns may either comprise removable yarns (e.g., yarns which are capable of removal from the fabric through combustion or dissolution) or tearable yarns (i.e., yarns which have a low tear strength relative to the yarns of the adjacent connected fabrics and may therefore be selectively torn from the fabric). Either type of connecting yarn is knitted into the fabric in a manner such that the fabric yarns form separate strips connected by the connecting yarns.

When the casting material is a fiberglass fabric, suitable removable connecting yarns are made of fibers which are combustible at temperatures lower than the degradation temperature of the inorganic fibers (e.g., glass fibers) of the connected fabric. Preferably the combustion temperature of the removable connecting yarn is less than the temperature commonly used for heat setting fiberglass yarns. More preferably the combustion temperature of the removable connecting yarn is between about 200° C. and 540° C. Most preferably the combustion temperature of the removable connecting yarn is between about 300° C. and 540° C. Heating the fabric to temperatures above about 540° C. should be avoided as subjecting the fiberglass to temperatures of greater than about 540° C. can weaken the fiberglass yarns in the fabric which may result in reduced strength of casts made from such fabrics. Preferably the tape is not heated above 480° C.

Furthermore, in order to avoid localized degradation of the fabric, the removable connecting yarn is also preferably a low denier yarn. It is presently believed that high denier and/or high heat of combustion yarns generate high localized heating during their combustion. These high localized heating should be avoided. Preferably the yarn is less than 500 denier. More preferably the yarn is less than 250 denier. Most preferably the yarn is less than 100 denier.

Alternatively, the removable connecting yarn may comprise fibers which are capable of dissolving in a gas or solution which doesn't dissolve the connected fabrics. A suitable removable yarn may be made of poly(vinyl alcohol) fibers which may be dissolved in water. Another suitable dissolvable yarn may be made of acetate fibers which may be dissolved in acetone. Acetate yarns are preferred because acetone is readily removed from the fabric and doesn't interfere with water-curable isocyanate-terminated polyurethane prepolymer coatings. Other dissolving yarns may also be employed.

Furthermore, it is preferred that the connecting yarn not undergo excessive shrinkage during the removal process. It is presently believed that excessive shrinkage prior to removal or during the removal process could distort the fabric. Preferably the yarn has less than about 25% shrinkage. More preferably the yarn has less than about 10% shrinkage. Most preferably the yarn has less than about 5% shrinkage.

Suitable tearable connecting yarns comprise fibers which have a suitably low tensile strength such that the tearable connecting yarn easily tears when a tensile force is applied. The tearable yarn should have a sufficiently low tear strength, relative to the yarns which form the connected fabrics, such that the tearable yarn tears before the fabric yarns. The tearable connecting yarn should be strong enough to hold the connected fabric strips together during processing and during normal use prior to the tearing operation. Suitable fabric yarns for use in this invention have a tensile strength of at least about 2 kg. Preferably the fabric yarns have a tensile strength of between about 2 and about 3 kg. Preferably the tearable connecting yarns have a tensile strength of between about 5% and 50% of the tensile strength of the fabric yarns. Most preferably the tearable connecting yarns have a tensile strength of between about 10% and 25% of the tensile strength of the fabric yarns.

Alternatively, when the fabric comprises inorganic yarns, a tearable connecting yarn may comprise both inorganic and organic fibers (e.g., a blend of a small number of inorganic fibers with a larger number of organic fibers). A blend yarn has the advantage that the organic fibers provide strength to the yarn during knitting but may be selectively burned out during the heat-setting process to facilitate tearing. Upon removal of the organic portion of the connecting yarn, the inorganic fibers of the blended connecting yarn connect the fabric halves of the tape. This yarn tears more easily than the stronger inorganic yarns due to its smaller bundle count. Preferably the blended connecting yarns have a tensile strength, after removal of the organic fibers, of between about 5% and 50% of the tensile strength of the inorganic yarns. Most preferably the tearable connecting yarns have a tensile strength, after removal of the organic fibers, of between about 10% and 25% of the tensile strength of the inorganic yarns.

In one embodiment, the fabric of the present invention is knit with connecting yarns and inorganic fabric yarns. When used as a removable connecting yarn the connecting yarn is preferably organic and is selectively knitted into the fabric at intervals along the width of the fabric such that the fabric comprises two or more separate strips of inorganic fabric connected by the organic yarn(s). Preferably, fabrics of the present invention (when in the connected form) are wider than about 50 mm prior to removal of the organic connecting yarn(s). More preferably, fabrics of the present invention (when in the connected form) are wider than about 100 mm prior to removal of the organic connecting yarn(s). Very wide fabric rolls (when in the connected form) might inhibit the air flow and/or heat transfer in a convection oven. Care should be taken to ensure proper ventilation and heat capacity when heat desizing very wide connected rolls. Preferably, after removal of the organic connecting yarn(s), the narrow fabric is less than 50 mm wide. More preferably, after removal of the organic connecting yarn(s), the narrow fabric is less than 30 mm wide.

The removable connecting yarn(s) may be knit into the fabric either as a laid-in stitch or as a chain stitch. Preferably, the removable connecting yarn(s) is knit into the fabric as a laid-in stitch. The essential requirements of a connecting yarn are that it be capable of knitting with the fabric yarn and connect two fabrics. Therefore, when the connecting yarn is removed, e.g., through combustion or dissolution, the fabric remains present in the form of two or more narrower fabric strips.

When the removable connecting yarn is present as laid-in yarns it is preferably present as two or more parallel laid-in yarns. While one laid-in yarn is perfectly acceptable, it has been found that two or more adjacent and parallel removable laid-in yarns provides better control of the fabric prior to removal. Most preferably, three parallel laid-in yarns form the connecting yarn.

The removable connecting yarn may also be a chain stitch yarn. When the removable connecting yarn is knitted in the form of a chain stitch it is necessary that the fabric laid-in yarns not bridge the connecting yarn and connect the two adjacent fabric chain stitch yarns. Were this construction formed, the fabric would not separate into two narrower fabrics upon the removal of the removable connecting yarn. When the removable connecting yarn is knitted in the form of a chain stitch the resulting fabric has extended loops on the edge of the fabric where the chain stitch has been removed.

When used as a tearable connecting yarn the tearable connecting yarn is preferably organic and is selectively knitted into the fabric at intervals along the width of the fabric such that the fabric comprises two or more separate strips of inorganic fabric connected by the tearable organic yarn(s). Preferably, fabrics of the present invention have tearable connecting yarns at less than about 50 mm intervals. More preferably, fabrics of the present invention have tearable connecting yarns at about 25 mm intervals. The exact position of the tearable connecting yarns may be adjusted depending on the width of the fabric or the intended application of the casting tape. To facilitate tearing it may be desirable to color (e.g., pigment or dye) the tearable yarn a contrasting color from the higher strength fabric yarns. This will allow the user more easily to focus stress at the tearable yarn during the tearing step.

The tearable connecting yarn may be knit into the fabric either as a laid-in stitch or as a chain stitch. Preferably, the tearable connecting yarn is knitted into the fabric as a laid-in stitch. The essential requirements of a connecting yarn are that it be capable of knitting with the fabric yarn and connect two fabrics. Therefore, when the connecting yarn is torn the fabric remains present in the form of two or more narrower fabric strips.

When the tearable connecting yarn is present as laid-in yarns it is preferably present as one yarn. Two or more parallel yarns may also be utilized but are not preferred.

The tearable yarn may also be present as a chain stitch yarn although this is not preferred. When the tearable connecting yarn is knitted in the form of a chain stitch it is necessary that the fabric laid-in yarns not bridge the connecting yarn and connect the two adjacent fabric chain stitch yarns. Were this construction formed, the fabric would not tear easily into two narrower fabrics.

In processing the knitted fiberglass fabric of the present invention, a length of fabric is optionally, and preferably, heat-set with essentially no tension. Preferably, the fabric is wound onto a cylindrical core so large batches can be processed at one time in a single oven. Care must be taken to avoid applying undue tension to the fabric which would distort the knots and loops. A continuous heat-setting process may also be used in which a length of fabric is placed without undue tension on a moving conveyor system and passed through an oven for sufficient time and temperature to achieve heat setting of the fabric.

The heat-setting step may be performed in a number of conventional ways known to the art. In heat-setting a small piece of fabric, e.g., 25 centimeters of tape, in a single layer, a temperature of 425° C. for three minutes has been found to be sufficient. To achieve optimum setting, a temperature of 540° C. for three minutes is required. Equivalent setting at lower temperatures is possible, but longer time is required. Batch processes require a longer residence time at the selected temperature due to the mass of glass fabric which must be heated.

The optimum heat-setting process described above is sufficient in most cases to remove the sizing from the fabric. However, the process of the present invention may also be practiced using partially heat-desized or a chemically-desized fabric. Chemical desizing processes are described in U.S. Pat. Nos. 3,686,725; 3,787,272; and 3,793,686. Heat desizing processes are described in U.S. Pat. No. 4,609,578.

The fabric is preferably cooled prior to application of the resin. The resin selected to apply to the heat-set fabric is dictated by the end-use of the product. For orthopedic casting materials, suitable resins are well-known and described for example, in U.S. Pat. Nos. 4,376,438; 4,433,680; 4,502,479; and 4,667,661 which are herein incorporated by reference. The preferred resins are the moisture-curable isocyanate-terminated polyurethane prepolymers described in the aforementioned patents. The amount of such resin applied to the fiberglass tape to form an orthopedic casting material is typically an amount sufficient to constitute 35 to 50 percent by weight of the final "coated" tape. The term "coated" or "coating" as used herein with respect to the resin refers generically to all conventional processes for applying resins to fabrics and is not intended to be limiting. In the case of tearable yarns, it is desirable that the tearable yarns not swell or dissolve in the resin.

To insure storage stability of the coated tape, it must be properly packaged, as is well known in the art. In the case of water-curable isocyanate-terminated polyurethane prepolymer resin systems, moisture must be excluded. This is typically accomplished by sealing the tape in a foil or other moisture-proof pouch.

In addition to the application of the present invention to the field of orthopedic casting tapes, other uses may include wrapping and/or joining pipes, cables or the like; patching or bridging gaps to provide a surface for filling and repairs; etc.

The invention may be further illustrated by the following working examples which are merely illustrative and not intended to be limiting in any way.

EXAMPLE 1

Preparation of a Narrow Casting Tape

Fiberglass tape was knit on a two bar Raschel warp knitter using fiberglass yarn (ECDE 75 1/0.7Z Sizing PPG610; available from PPG Industries Inc.) and polyester connecting yarn (1/70/34 T-56 dyed polyester yarn; available from UNIFI, Inc.). The fabric was a two bar, 18 gauge construction consisting of an open chain stitch and a layin stitch which overlaps 4 needles. The fabric characteristics are: 0.5 wales per mm; 0.6 courses per mm; chain stitch runner length of 3.73 meters (m); layin stitch runner length of 3.7 meters. A relaxed section of tape 254 mm in length can be extended to a length of 337 mm when manually held taut (32.5% stretch).

The tape was 71 mm wide as knit. Three polyester yarns were knit as layin stitch yarns, in place of fiberglass yarns, at the midpoint of the tape. The polyester connecting yarns were tensioned at 5 gm. This amount of tension was sufficient to hold the two narrower webs together yet not an excessive amount which would deform the webs. The tape was then wound on a metal core into a roll which contains about 412 meters of tape. The winding operation was performed with a sag in the tape as it was rolled onto the core. Therefore, there was essentially no tension applied to the tape. The loose roll of fiberglass tape (with polyester connecting yarns) was then placed in a cool oven. The oven was closed and set to reach 421° C. within 1 hour. After 8 hours the heat was turned off and the oven, while remaining closed, was allowed to cool to 360° C. The oven was then opened and further allowed to cool to 240° C. The tape was then removed from the oven in the form of two separate narrower rolls with a gap where the now combusted polyester yarns had been. The rolls were separately placed on a motorized spindle, and the tape was fed over a roller and 3.6 meters of tape was rewound on a core. At the roller station a liquid isocyanate-terminated polyurethane prepopolymer resin was extruded onto the tape so that the coated tape has 42.5% by weight resin. The unwind and windup tensions were adjusted to a minimum but no sag was present. The rolling operation was also under minimum tension so the coated tape was not stretched as it was taken up by the core. The roll of tape was then packaged in a plastic/aluminum laminate pouch impervious to water which was then heat-sealed. Tape removed from the pouch exhibits 30% extensibility in the lengthwise direction.

EXAMPLE 2

Preparation of a Narrow Organic Casting Tape

Polyester tape is knit on a two bar Raschel warp knitter using polyester fabric yarn and acetate connecting yarn. The fabric is a two bar, 18 gauge construction consisting of an open chain stitch and a layin stitch which overlaps 4 needles. The fabric characteristics are: 0.5 wales per mm; 0.6 courses per mm; chain stitch runner length of 3.73 meters (m); layin stitch runner length of 3.7 meters.

The tape is 71 mm wide as knit. Three acetate yarns are knit as layin stitch yarns, in place of polyester yarns, at the midpoint of the tape. The acetate connecting yarns are tensioned at 5 gm. This amount of tension is sufficient to hold the two narrower webs together yet not an excessive amount which would deform the webs. After knitting, the tape is passed through an acetone solvent bath to dissolve the acetate connecting yarns and thereby separate the fabric into two narrower fabrics. The acetone is then recovered from the tape by an evaporation process and a liquid isocyanate-terminated polyurethane prepopolymer resin is extruded onto the tape to form a narrow casting tape. The roll of tape is then packaged in a plastic/aluminum laminate pouch impervious to water which is then heat-sealed.

EXAMPLE 3

Preparation of a Narrow Inorganic Casting Tape

Fiberglass tape is knit on a two bar Raschel warp knitter using fiberglass fabric yarn and polyvinyl alcohol ("PVA") connecting yarn. The fabric is a two bar, 18 gauge construction consisting of an open chain stitch and a layin stitch which overlaps 4 needles. The fabric characteristics are: 0.5 wales per mm; 0.6 courses per mm; chain stitch runner length of 3.73 meters (m); layin stitch runner length of 3.7 meters.

The tape is 71 mm wide as knit. Three PVA yarns are knit as layin stitch yarns, in place of fiberglass yarns, at the midpoint of the tape. The PVA connecting yarns are tensioned at 5 gm. This amount of tension is sufficient to hold the two narrower webs together yet not an excessive mount which would deform the webs. After knitting, the tape is passed through an aqueous solvent bath to: (1) dissolve the PVA connecting yarns; (2) desize the fiberglass yarns; and (3) thereby separate the fabric into two narrower fabrics. The solvent is then recovered from the tape by an evaporation and drying process and a liquid isocyanate-terminated polyurethane prepopolymer resin is extruded onto the tape to form a narrow casting tape. The roll of tape is then packaged in a plastic/aluminum laminate pouch impervious to water which is then heat-sealed.

EXAMPLE 4

Preparation of a Tearable Organic Casting Tape

Polyester tape is knit on a two bar Raschel warp knitter using polyester fabric yarn and cotton connecting yarn. The fabric is a two bar, 18 gauge construction consisting of an open chain stitch and a layin stitch which overlaps 4 needles. The fabric characteristics are: 0.5 wales per mm; 0.6 courses per mm; chain stitch runner length of 3.73 meters (m); layin stitch runner length of 3.7 meters.

The tape is 71 mm wide as knit. Three cotton yarns are knit as layin stitch yarns, in place of polyester yarns, at the midpoint of the tape. The cotton connecting yarns are tensioned at 5 gm. This amount of tension is sufficient to hold the two narrower webs together yet not an excessive amount which would deform the webs or tear the cotton yarn. After knitting, the tape is coated with an isocyanate-terminated polyurethane prepopolymer resin to form a casting tape. The roll of tape is then packaged in a plastic/aluminum laminate pouch impervious to water which is then heat-sealed. Tape removed from the pouch exhibits good extensibility in the lengthwise direction and may be easily torn lengthwise to form two narrower fabric strips.

EXAMPLE 5

Preparation of a Tearable Inorganic Casting Tape

Fiberglass tape is knit on a two bar Raschel warp knitter using fiberglass yarn (ECDE 75 1/0.7Z Sizing PPG610; available from PPG Industries Inc.) and a blend of fiberglass and polyester connecting yarn (comprising 10% glass fibers and 90% polyester fibers). The fabric is a two bar, 18 gauge construction consisting of an open chain stitch and a layin stitch which overlaps 4 needles. The fabric characteristics are: 0.5 wales per mm; 0.6 courses per mm; chain stitch runner length of 3.73 meters (m); layin stitch runner length of 3.7 meters. A relaxed section of tape 254 mm in length can be extended to a length of 337 mm when manually held taut (32.5% stretch).

The tape is 71 mm wide as knit. Three blend yarns are knit as layin stitch yarns, in place of fiberglass yarns, at the midpoint of the tape. The blend connecting yarns are tensioned at 5 gm. This amount of tension is sufficient to hold the two narrower webs together yet not an excessive amount which would deform the webs. The tape is then wound on a metal core into a roll which contains about 412 meters of tape. The winding operation is performed with a sag in the tape as it was rolled onto the core. Therefore, there is essentially no tension applied to the tape. The loose roll of fiberglass tape (with blend connecting yarns) is then placed in a cool oven. The oven is closed and set to reach 421° C. within 1 hour. After 8 hours the heat is turned off and the oven, while remaining closed, is allowed to cool to 360° C. The oven is then opened and further allowed to cool to 240° C. The tape is then removed from the oven in the form of a wide roll with a smaller bundle count inorganic connecting yarn where the now combusted polyester fibers had been. The roll is placed on a motorized spindle, and the tape is fed over a roller and 3.6 meters of tape is rewound on a core. At the roller station a liquid isocyanate-terminated polyurethane prepopolymer resin is extruded onto the tape so that the coated tape has 42.5% by weight resin. The unwind and windup tensions are adjusted to a minimum but no sag is present. The rolling operation is also under minimum tension so the coated tape is not stretched as it is taken up by the core. The roll of tape is then packaged in a plastic/aluminum laminate pouch impervious to water which is then heat-sealed. Tape removed from the pouch exhibits 30% extensibility in the lengthwise direction and may be easily torn lengthwise to form two narrower fabric strips.

What is claimed is:

1. A method, comprising the steps of:

knitting a fiberglass fabric comprising at least one tearable connecting yarn of sufficient strength to hold the fabric together during processing and normal use in the warp direction of the fabric and a plurality of fiberglass fabric yarns; and coating said fabric with a moisture-curable isocyanate-terminated polyurethane prepolymer, wherein said coated fiberglass fabric is in the form of an orthopedic casting tape and said tearable connecting yarns may be readily torn thereby separating said casting tape into narrower strips.

2. The method according to claim 1, wherein said tearable connecting yarn is knit into said fiberglass fabric at less than about 50 mm intervals.

3. The method according to claim 1, wherein said tearable connecting yarn is knit into said fiberglass fabric at less than about 25 mm intervals.

4. The method according to claim 1, wherein said tearable connecting yarn has a tensile strength of between about 5% and 50% of the tensile strength of said fiberglass yarns.

5. An inorganic, resin coated fabric comprising:

a knit fabric sheet comprising at least one tearable connecting yarn of sufficient strength to hold the fabric together during processing and normal use in the warp direction of the fabric and a plurality of inorganic fabric yarns, wherein said inorganic fabric yarns are knit as two or more narrower fabric strips connected by said connecting yarn; and a curable resin coated on said fabric, wherein said resin coated fabric is in the form of an orthopedic casting tape and said tearable connecting yarn may be readily torn thereby separating said casting tape into narrower strips.

6. A fabric according to claim 5, wherein said tearable connecting yarn is selected from the group consisting of acetate, azlon, rayon, triacetate, acrylic, amid, nylon, poly(1-butene), polyethylene, poly(3-methyl-1-butene), poly(1-pentene), polypropylene, polystyrene, polyester, polytetrafluoroethylene, poly(vinyl alcohol), poly(vinyl chloride), poly(vinylidine chloride), abaca, cotton, flax, hemp, jute, kapok, linen, ramie, sisal, wool, mohair, vicuna, and silk.

7. A fabric according to claim 5, wherein said fabric has tearable connecting yarns at less than about 50 mm intervals.

8. A fabric according to claim 5, wherein said fabric has tearable connecting yarns at less than about 25 mm intervals.

9. A fabric according to claim 5, wherein said inorganic fabric yarn is fiberglass; and said wide fabric is coated with a moisture-curable isocyanate-terminated polyurethane prepolymer.

10. A narrow knit fiberglass fabric comprising:

at least one removable connecting yarn in the warp direction of the fabric, said removable connecting yarn being combustible; and a plurality of fiberglass fabric yarns which resist combustion, said connected knit fabric formed into a wide roll and said connecting yarn combusted from said wide roll to thereby separate said roll into two or more rolls of narrower fiberglass fabric, wherein at least one of said narrow fiberglass fabrics is less than about 50 mm wide after the removable connecting yarn has been removed.

11. A narrow knit fiberglass fabric comprising:

at least one removable connecting yarn in the warp direction of the fabric, said removable connecting yarn being dissoluble or combustible, wherein said removable connecting yarn is knit into said fabric as one or more laid-in stitches, said laid-in stitches connecting two or more fabrics; and a plurality of fiberglass fabric yarns, said connected knit fabric formed into a wide roll and said connecting yarn combusted or dissolved from said wide roll to thereby separate said roll into two or more rolls of narrower fiberglass fabric, wherein at least one of said narrow fiberglass fabrics is less than about 50 mm wide after the removable connecting yarn has been removed.

12. A narrow knit fiberglass fabric comprising a plurality of fiberglass fabric yarns and at least one removable connecting yarn in the warp direction of the fabric, said removable connecting yarn being dissoluble or combustible, said connected knit fabric formed into a wide roll and said connecting yarn combusted or dissolved from said wide roll to thereby separate said roll into two or more rolls of narrower fiberglass fabric, wherein at least one of said narrow fiberglass fabrics is less than about 50 nun wide after the removable connecting yarn has been removed, and wherein said narrow fabric is coated with a moisture-curable isocyanate-terminated polyurethane prepolymer.

* * * * *

UNITED STATES PATENT AND TRADEMARK OFFICE
CERTIFICATE OF CORRECTION

PATENT NO.: 5,507,079

DATED: April 16, 1996

INVENTOR(S): Jacqueline A. Schmidt, John M. Kokorudz, Matthew T. Scholz, Miroslav M. Tochacek and F. Andrew Ubel III It is certified that error appears in the above-identified patent and that said Letters Patent is hereby corrected as shown below:

Col. 1, line 15, "tom" should read -- torn --.

Col. 1, line 40, after the second instance of the word "fibers" insert --exhibit--

Col. 3, line 42, "tom" should read -- torn --.

Col. 3, line 47, "tom" should read -- torn --.

Col. 8, line 37, "tom" should read -- torn --.

Col. 10, line 67, "mount" should read -- amount --.

Col. 11, line 35, "tom" should read -- torn --.

Col. 14, line 16, "nun" should read -- mm --.

Signed and Sealed this

Fifth Day of May, 1998

*Attest:*

BRUCE LEHMAN

*Attesting Officer*     Commissioner of Patents and Trademarks